(12) United States Patent
Hammer

(10) Patent No.: US 8,870,922 B2
(45) Date of Patent: Oct. 28, 2014

(54) CLAMP FOR SPINAL CROSS CONNECTING DEVICE

(75) Inventor: Michael Hammer, Pine Brook, NJ (US)

(73) Assignee: Blackstone Medical, Inc., Lewisville, TX (US)

( * ) Notice: Subject to any disclaimer, the term of this patent is extended or adjusted under 35 U.S.C. 154(b) by 175 days.

(21) Appl. No.: 13/442,762

(22) Filed: Apr. 9, 2012

(65) Prior Publication Data

US 2012/0259369 A1    Oct. 11, 2012

Related U.S. Application Data

(60) Provisional application No. 61/473,004, filed on Apr. 7, 2011.

(51) Int. Cl.
*A61B 17/70* (2006.01)
(52) U.S. Cl.
CPC ......... *A61B 17/7049* (2013.01); *A61B 17/7052* (2013.01)
USPC ............................ 606/251; 606/250; 606/253
(58) Field of Classification Search
CPC ........... A61B 17/7049; A61B 17/7052; A06B 17/705
USPC .......... 606/250–253, 260, 276–278, 324, 151
See application file for complete search history.

(56) References Cited

U.S. PATENT DOCUMENTS

| | | |
|---|---|---|
| 4,046,344 A | 9/1977 | Scanlan |
| 5,520,689 A | 5/1996 | Schlapfer et al. |
| 5,527,310 A | 6/1996 | Cole et al. |
| 5,669,910 A | 9/1997 | Korhonen et al. |
| 6,217,578 B1 | 4/2001 | Crozet et al. |
| 6,264,658 B1 | 7/2001 | Lee et al. |
| 6,302,882 B1 | 10/2001 | Lin et al. |
| 6,309,390 B1 | 10/2001 | Le Couedic et al. |
| 6,540,748 B2 | 4/2003 | Lombardo |
| 6,547,790 B2 | 4/2003 | Harkey, III et al. |
| 6,595,992 B1 | 7/2003 | Wagner et al. |
| 6,699,248 B2 | 3/2004 | Jackson |
| 6,752,807 B2 | 6/2004 | Lin et al. |

(Continued)

FOREIGN PATENT DOCUMENTS

| EP | 0572790 B1 | 2/1996 |
|---|---|---|
| WO | 2007041085 A1 | 4/2007 |

OTHER PUBLICATIONS

U.S. Office Action, U.S. Appl. No. 13/341,636, dated Jun. 18, 2013, 7 pages.

(Continued)

*Primary Examiner* — Pedro Philogene
*Assistant Examiner* — Christina Negrellirodrigue
(74) *Attorney, Agent, or Firm* — Baker & McKenzie LLP

(57) ABSTRACT

A clamp for attaching a cross connecting device to a spinal fixation system comprising an outer body and an inner body. The outer body defines an internally threaded bore and an outer body cavity, and the inner body defines an inner body cavity. The inner body is at least partially disposed within the outer body. A pin is provided for connecting the inner and outer bodies to each other, while allowing for a limited amount of movement therebetween. A set screw suitable for being driven into the internally threaded bore is provided for securing the inner body to the spinal fixation system.

22 Claims, 6 Drawing Sheets

(56) References Cited

U.S. PATENT DOCUMENTS

| | | |
|---|---|---|
| 6,783,526 B1 | 8/2004 | Lin et al. |
| 6,866,664 B2 | 3/2005 | Schar et al. |
| 7,066,938 B2 | 6/2006 | Slivka et al. |
| 7,160,301 B2 | 1/2007 | Cordaro |
| 7,232,441 B2 | 6/2007 | Altarac et al. |
| 7,270,665 B2 | 9/2007 | Morrison et al. |
| 7,344,537 B1 | 3/2008 | Mueller |
| 7,481,827 B2 | 1/2009 | Ryan et al. |
| 7,621,942 B2 | 11/2009 | Piehl |
| 7,645,294 B2 | 1/2010 | Kalfas et al. |
| 7,695,500 B2 | 4/2010 | Markworth |
| 7,717,939 B2 | 5/2010 | Ludwig et al. |
| 7,918,876 B2 | 4/2011 | Mueller et al. |
| 8,025,679 B2 | 9/2011 | Nichols et al. |
| 2003/0045874 A1 | 3/2003 | Thomas, Jr. |
| 2003/0114853 A1 | 6/2003 | Burgess et al. |
| 2003/0130661 A1 | 7/2003 | Osman |
| 2004/0133203 A1 | 7/2004 | Young et al. |
| 2005/0090821 A1 | 4/2005 | Berrevoets et al. |
| 2005/0228326 A1 | 10/2005 | Kalfas et al. |
| 2005/0228377 A1 | 10/2005 | Chao et al. |
| 2006/0058789 A1 | 3/2006 | Kim et al. |
| 2006/0064093 A1 | 3/2006 | Thramann et al. |
| 2006/0235392 A1 | 10/2006 | Hammer et al. |
| 2006/0271051 A1 | 11/2006 | Berrevoets et al. |
| 2007/0016197 A1 | 1/2007 | Woods et al. |
| 2007/0118121 A1 | 5/2007 | Purcell et al. |
| 2007/0213723 A1 | 9/2007 | Markworth et al. |
| 2008/0021456 A1 | 1/2008 | Gupta et al. |
| 2008/0086134 A1 | 4/2008 | Butler et al. |
| 2008/0091205 A1 | 4/2008 | Kuiper et al. |
| 2008/0109039 A1 | 5/2008 | Michielli et al. |
| 2008/0125781 A1 | 5/2008 | Hoffman et al. |
| 2008/0147123 A1 | 6/2008 | Schermerhorn |
| 2008/0172093 A1 | 7/2008 | Nilsson |
| 2008/0177314 A1 | 7/2008 | Lemoine |
| 2008/0177315 A1 | 7/2008 | Usher |
| 2009/0210007 A1* | 8/2009 | Levy et al. .................. 606/246 |
| 2009/0270924 A1 | 10/2009 | Wing et al. |
| 2009/0312801 A1 | 12/2009 | Lemoine et al. |
| 2010/0010541 A1 | 1/2010 | Boomer et al. |
| 2010/0094345 A1 | 4/2010 | Saidha et al. |
| 2010/0152776 A1 | 6/2010 | Keyer et al. |
| 2010/0204733 A1 | 8/2010 | Rathbun et al. |
| 2010/0222779 A1 | 9/2010 | Ziemek et al. |
| 2010/0256681 A1 | 10/2010 | Hammer et al. |
| 2010/0324557 A1 | 12/2010 | Cheema et al. |
| 2011/0034956 A1* | 2/2011 | Mazda et al. .................. 606/278 |
| 2011/0190824 A1 | 8/2011 | Gephart et al. |

OTHER PUBLICATIONS

U.S. Notice of Allowance, U.S. Appl. No. 13/341,587, dated Jun. 13, 2013, 10 pages.

International Search Report and Written Opinion, PCT/US2012/072107, 9 pages, dated Mar. 1, 2013.

International Search Report & Written Opinion, PCT/US2012/072110, dated Mar. 15, 2013, 9 pages.

International Search Report and Written Opinion, PCT/US2012/032805, dated Aug. 3, 2012, 8 pages.

* cited by examiner

CLAMP FOR SPINAL CROSS CONNECTING DEVICE

PRIORITY TO RELATED APPLICATIONS

The present application claims priority to U.S. Provisional Patent Application No. 61/473,004 entitled "CLAMP FOR SPINAL CROSS CONNECTION DEVICE," which was filed on Apr. 7, 2011, and is hereby incorporated by reference in its entirety.

BACKGROUND

1. Technical Field

The present application relates to connection systems for spinal fixation devices, including cross connecting devices for spinal fixation bone anchors such as bone screws and hooks.

2. Related Art

The bones and connective tissue of an adult human spinal column includes more than twenty vertebrae coupled sequentially to one another by a tri-joint complex. The complex includes an anterior disc and two posterior facet joints. The anterior discs of adjacent bones are cushioned by cartilage spacers referred to as intervertebral discs. The vertebrae are each anatomically categorized into one of four classifications: cervical, thoracic, lumbar, and sacral. The cervical portion of the spine, which comprises the top of the spine up to the base of the skull, includes the first seven vertebrae. The intermediate twelve vertebrae are thoracic vertebrae, and connect to the lower spine comprising five lumbar vertebrae. The base of the spine includes the sacral bones (including the coccyx).

The spinal column is highly complex in that it includes over twenty vertebrae coupled to one another for housing and protecting critical elements of the nervous system. These elements of the nervous system have seemingly innumerable peripheral nerves and circulatory bodies in close proximity to each other. Despite its complexity, the spine is a highly flexible structure, capable of a high degree of curvature and twisting in many different directions.

However, genetic or developmental irregularities, trauma, chronic stress, tumors and disease can result in spinal pathologies that either limit this range of motion, or threaten the critical elements of the nervous system protected by the spinal column. A variety of systems have been disclosed in the art which provide some degree of immobilization of the spine by implanting artificial assemblies in or onto the spinal column. These assemblies include anterior, posterior, and lateral assemblies. Lateral and anterior assemblies can be coupled to the anterior portion of the spine, typically between vertebral bodies. Posterior spinal fixation systems generally include a pair of rods, which can be aligned along an axis to which the bones are to be disposed, and which are then attached to the spinal column by spinal fixation bone anchors, such as pedicle hooks and/or pedicle screws. Hooks can be coupled to the lamina or attached to transverse processes, while screws can be inserted through pedicles. In order to provide enhanced torsional rigidity, these structures can include cross-connecting devices for coupling the rods together in a direction that is generally transverse with respect to the axis of the rods. These cross-connecting devices can be coupled directly to the rods themselves, or can be attached to the bone anchors.

A number of improvements to prior cross-connecting devices are desirable. For example, it is desirable to provide clamps for cross-connecting devices that are highly adjustable in several degrees of freedom.

SUMMARY

Spinal fixation devices, cross connecting devices for spinal fixation devices, and components thereof, including clamps for cross connecting devices, are described herein.

According to one aspect of the present disclosure, a clamp for attaching a cross connecting device to a spinal fixation system comprises an outer body that defines an internally threaded bore and an outer body cavity, an inner body that is at least partially disposed within the outer body cavity, the inner body defining an inner body cavity, a pin for connecting the outer and inner bodies to each other, and a set screw suitable for being driven into the internally threaded bore for securing the inner body to the spinal fixation system.

The spinal fixation system can include a rod, and the outer body can include a clearance slot for allowing the rod to extend through the outer body cavity. The inner body can include a slotted rod-receiving interface. The slotted rod-receiving interface can include a rod-receiving portion configured to snap onto the rod. The rod-receiving portion of the slotted rod-receiving interface can be configured to be tightened onto the rod as the set screw is driven into the internally threaded bore. The slotted rod-receiving interface can further include at least one expansion portion.

The outer body can include a slot that extends between the internally threaded bore and the outer body cavity. The inner body can include a lever portion that extends through the slot into the internally threaded bore.

The clamp can further comprise a stop feature for limiting pivoting movement between the outer and inner bodies about the pin. The stop feature can include a tab and a mating groove.

According to another aspect of the present disclosure, a spinal fixation system can comprise a spinal fixation device, a rod connected to the spinal fixation device, a cross-connecting device, and a clamp for connecting the cross-connecting device to the rod. The clamp can comprise an outer body that defines an internally threaded bore and an outer body cavity, an inner body that is at least partially disposed within the outer body cavity, the inner body defining an inner body cavity configured to receive at least a portion of the spinal fixation device body, a pin for connecting the outer and inner bodies to each other, and a set screw suitable for being driven into the internally threaded bore for securing the inner body to the rod.

The outer body of the clamp can include a clearance slot for allowing the rod to extend through the outer body cavity. The inner body of the clamp can include a slotted rod-receiving interface. The slotted rod-receiving interface includes a rod-receiving portion can be configured to snap onto the rod. The rod-receiving portion of the slotted rod-receiving interface can be configured to be tightened onto the rod as the set screw is driven into the internally threaded bore. The slotted rod-receiving interface can further include at least one expansion portion.

The outer body of the clamp can include a slot that extends between the internally threaded bore and the outer body cavity. The inner body of the clamp can include a lever portion that extends through the slot into the internally threaded bore.

The clamp of the spinal fixation system can further comprise a stop feature for limiting pivoting movement between the outer and inner bodies about the pin. The stop feature can include a tab and a mating groove.

The spinal fixation device can include a spinal fixation device body, and the inner body can be configured to receive at least a portion of the spinal fixation device body.

These and other features, aspects, and embodiments of the invention are described below in the section entitled "Detailed Description."

BRIEF DESCRIPTION OF THE DRAWINGS

Features, aspects, and embodiments of the inventions are described in conjunction with the attached drawings, in which.

DETAILED DESCRIPTION

Figure 1A:
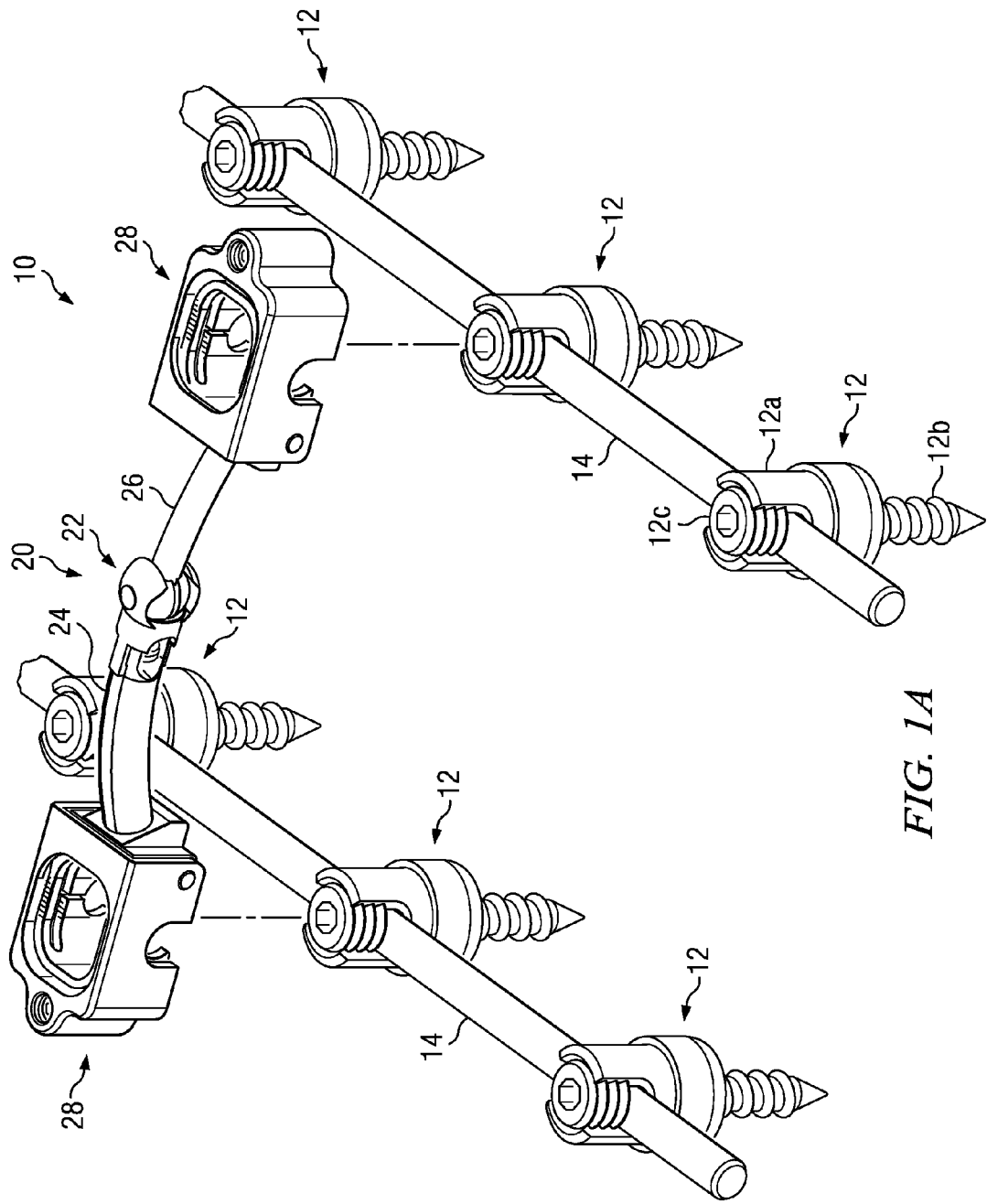
FIGS. 1A and 1B show a spinal fixation system having a cross connecting device that is attached to rods using clamps according to the present disclosure.
Figure 1B:
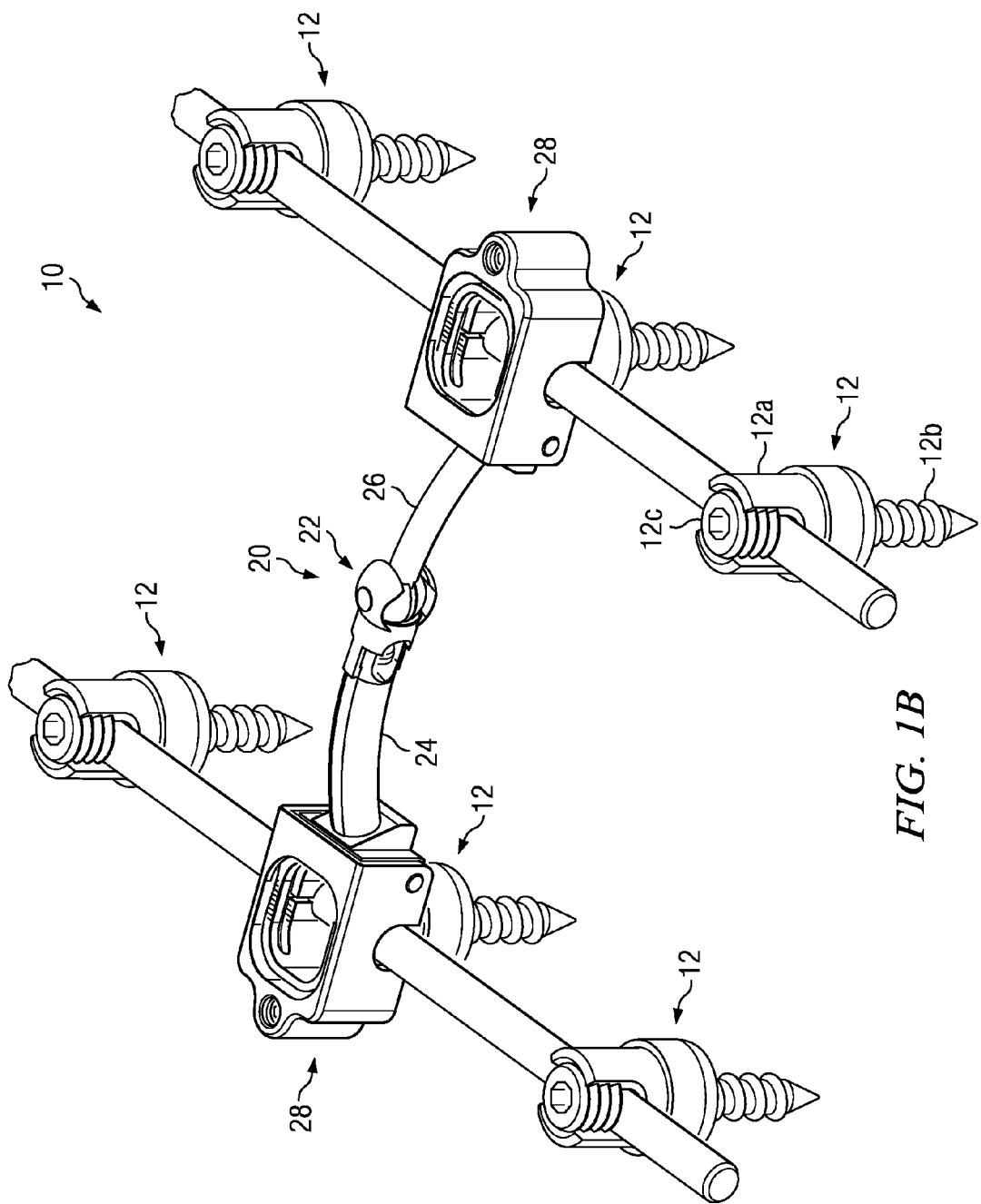

FIGS. 1A and 1B show a spinal fixation system 10 that includes a plurality of spinal fixation devices 12 and a pair of rods 14. A cross connecting device 20 is also provided for connecting opposing rods 14 and spinal fixation devices 12.

The spinal fixation devices 12 can include pedicle screws as shown, and can include other types of bone anchors, including hooks. Each fixation device 12 includes a body 12a, a shank 12b, and a set screw 12c. There are various known body styles, including the open style shown. Alternative styles include closed, reduction, and offset body styles. The shank 12b can be cannulated or non-cannulated. The shank 12b can be monoaxial or mutliaxial relative to the body 12a. Each shank 12b can include a single-lead thread as shown, or can include multiple-lead threads, where there are two or more threads that wind along the shank, usually equally spaced apart from each other. Instead of a shank 12b, one or more of the bodies 12a can include, or be attached to, a hook that can be attached to vertebrae, for example in the cervical area where vertebrae are small.

Once the spinal fixation devices 12 are secured to bone, the rods 14 can be placed along the bodies 12a and secured in place by the set screws 12c. Then, once the rods 14 are secured to the spinal fixation devices 12, the cross connecting device 20 can be placed over bodies 12a of a pair of spinal fixation devices 12 as shown in FIGS. 1A and 1B.

The cross connecting device 20 includes a fixable pivot junction 22, a first connection member 24, a second connection member 26, and clamps 28. The cross connecting device 20 can be lengthwise and angularly adjusted, thereby accommodating for translational, rotational, and angular misalignments between the connected spinal fixation devices 12. More specifically, the first and second connection members 24 and 26 are connected by the fixable pivot junction 22 such that the fixable pivot junction 22 allows the first and second connection members 24 and 26 to be translationally, rotationally, and angularly repositioned relative to each other. Once desired adjustments are made, the fixable pivot junction 22 can be locked, and the clamps 28 can be secured to the rods 14 as described in greater detail below.

Figure 2:
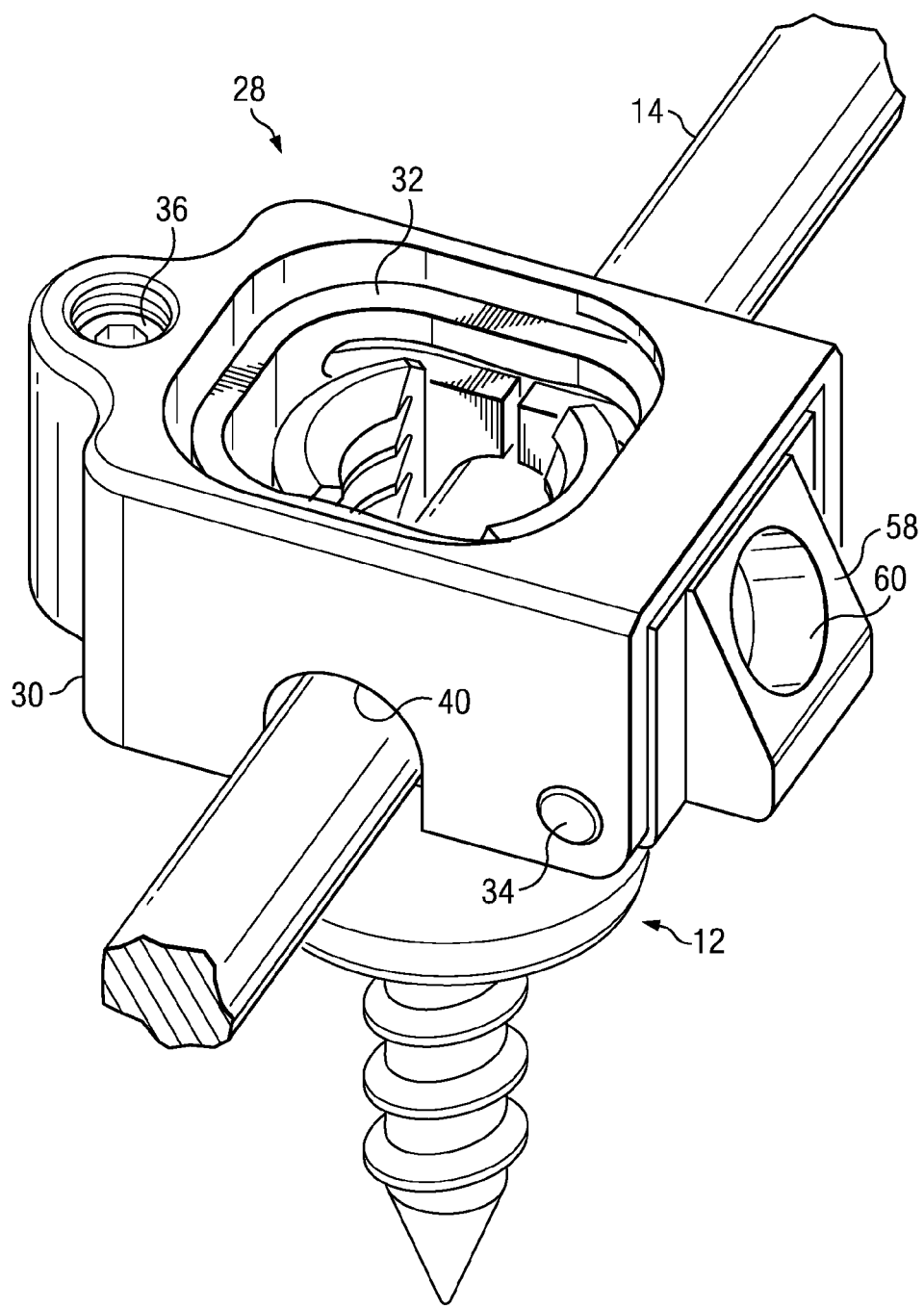
FIG. 2 shows an enlarged perspective view of the clamp attached to a body and rod of the spinal fixation device shown in FIGS. 1A and 1B.
Figure 3:
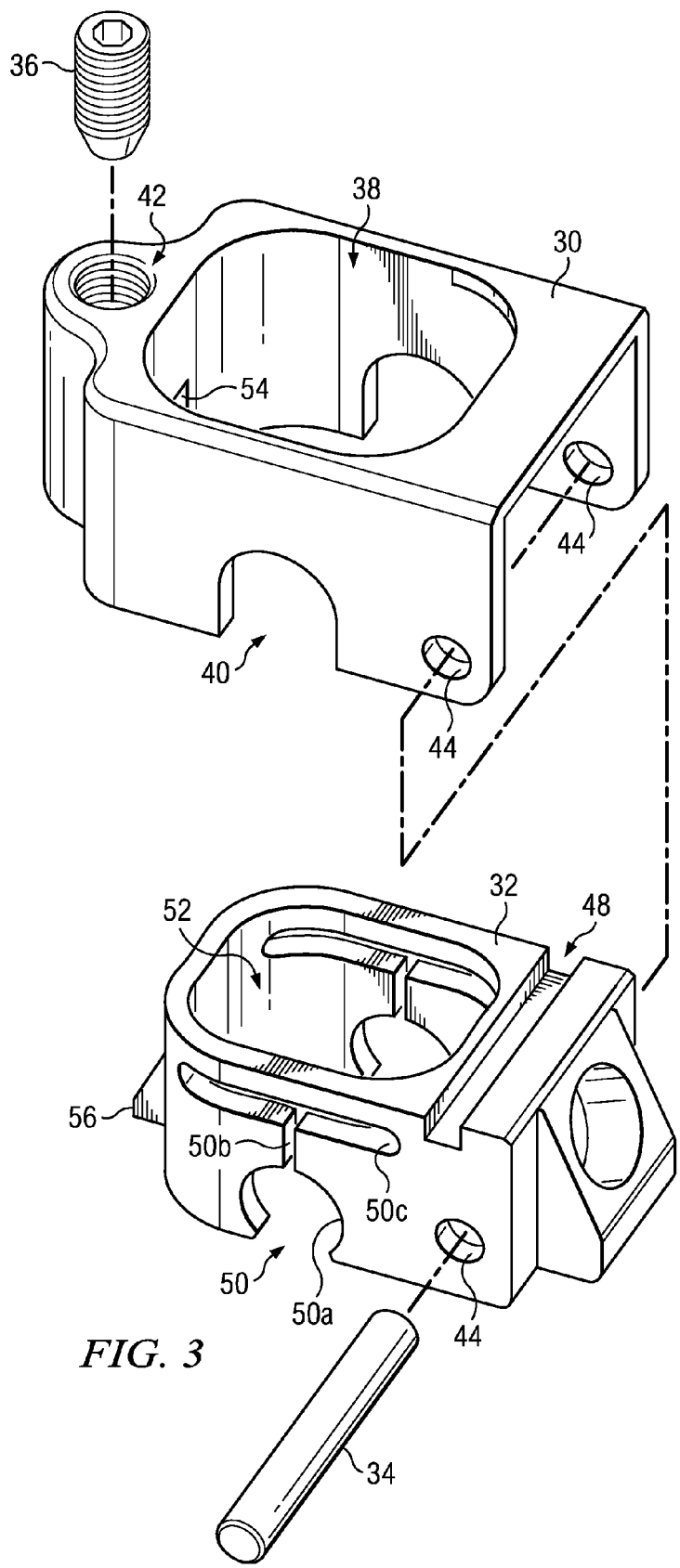
FIG. 3 shows an exploded view of the clamp shown in FIG. 2.
Figure 4:
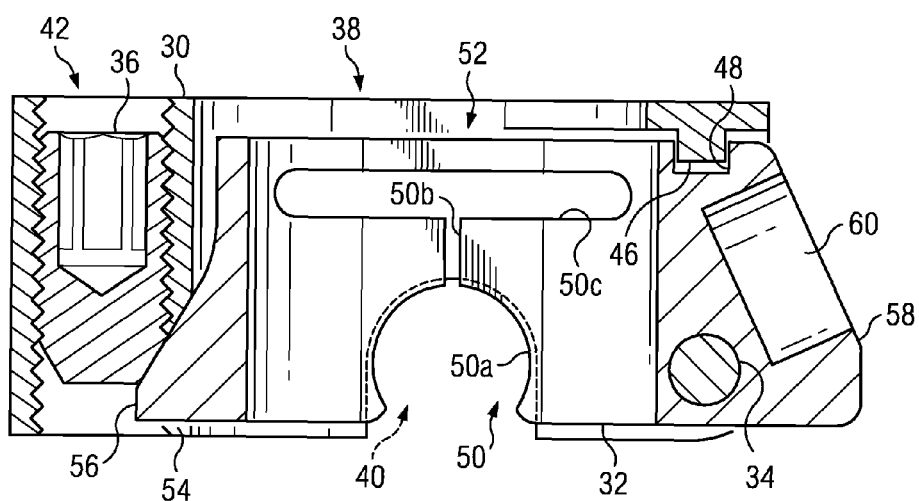
FIG. 4 shows a cross-sectional view of the clamp shown in FIGS. 2 and 3.

FIG. 2 shows an enlarged perspective view of a clamp 28 attached to the body 12a and rod 14 of the spinal fixation device 12. FIG. 3 shows an exploded view of the clamp 28, and FIG. 4 shows a cross-sectional view of the clamp 28. The clamp 28 includes an outer body 30, an inner body 32, a pin 34, and a set screw 36.

The outer body 30 includes an outer-body cavity 38 within which the inner body 32 resides. The outer body 30 also has a clearance slot 40 to allow the rod 14 to connect to the inner body 32. The outer body 30 also has an internally-threaded bore 42 for receiving the correspondingly-threaded set screw 36.

The outer body 30 and the inner body 32 are secured together by the pin 34. The outer and inner bodies 30 and 32 include pin holes 44 that are aligned and receive the pin 34. The pin holes 44 can be sized such that the pin 34 is press-fit into one or more of the pin holes 44 so that once the pin 34 is installed into the holes 44, it cannot easily be removed from the holes 44. An alternative type of connecting element can be used in place of the pin 34, such as a bolt or rivet.

The clamp 28 preferably includes a stop feature for preventing, or at least limiting, pivoting movement between the outer and inner bodies 30 and 32 about the pin 34. In the illustrated embodiment, a tab 46 on the underside of the outer body 30 engages a mating groove 48 of the inner body 32, thereby restricting the outer and inner bodies 30 and 32 from pivoting about the pin 34. Thus, the combination of the tab 46 and mating groove 48 constitute an embodiment of a stop feature. Alternatively, the tab 46 can be provided on the inner body 30 and the mating groove can be provided on the outer body 32, opposite the configuration shown. Other alternative embodiments can include a pin, rivet, bolt, or other device that can be used for restricting pivoting about the pin 34. Such alternatives can be used with, or in place of, the combination of the tab 46 and mating groove 48.

The inner body 32 has a slotted rod receiving interface 50. The interface 50 includes a rod-receiving portion 50a, a first expansion portion 50b, and a second expansion portion 50c. The rod-receiving portion 50a is defined by an at least somewhat circular geometry that is slightly smaller than the diameter of the rod 14 and is configured to snap onto the rod 14. The expansion portions 50b and 50c are provided above the rod-receiving portion 50a. The expansion portions 50b and 50c allow the rod-receiving portion 50a to expand without permanently deforming the inner body 32 as the clamp 28 is snapped onto a rod 14. The slightly undersized rod-receiving portion 50a results in a friction fit with the rod 14.

The inner body 32 has an inner-body cavity 52 that is configured to fit over a body 12a of a spinal fixation device 12. The fit between the inner body 32 and the body 12a of the spinal fixation device 12 is preferably such that a relatively small amount of clearance exists between them along the longitudinal axis of the rod 14, and that more substantial clearance exists in the medial region 52a and lateral region 52b (shown in FIG. 5) of the inner-body cavity 52. The additional clearance in the medial and lateral regions 52a and 52b allows for some variation in the orientation of the body 12a, for example in a plane perpendicular to the longitudinal axis of the rod 14.

The outer body 30 includes a slot 54 that extends between the threaded bore 42 and the outer-body cavity 38. The slot 54 provides an opening for a lever portion 56 of the inner body 32. The lever portion 56 is a protruding tapered geometry that extends into the threaded bore 42 through the slot 54.

Figure 5:
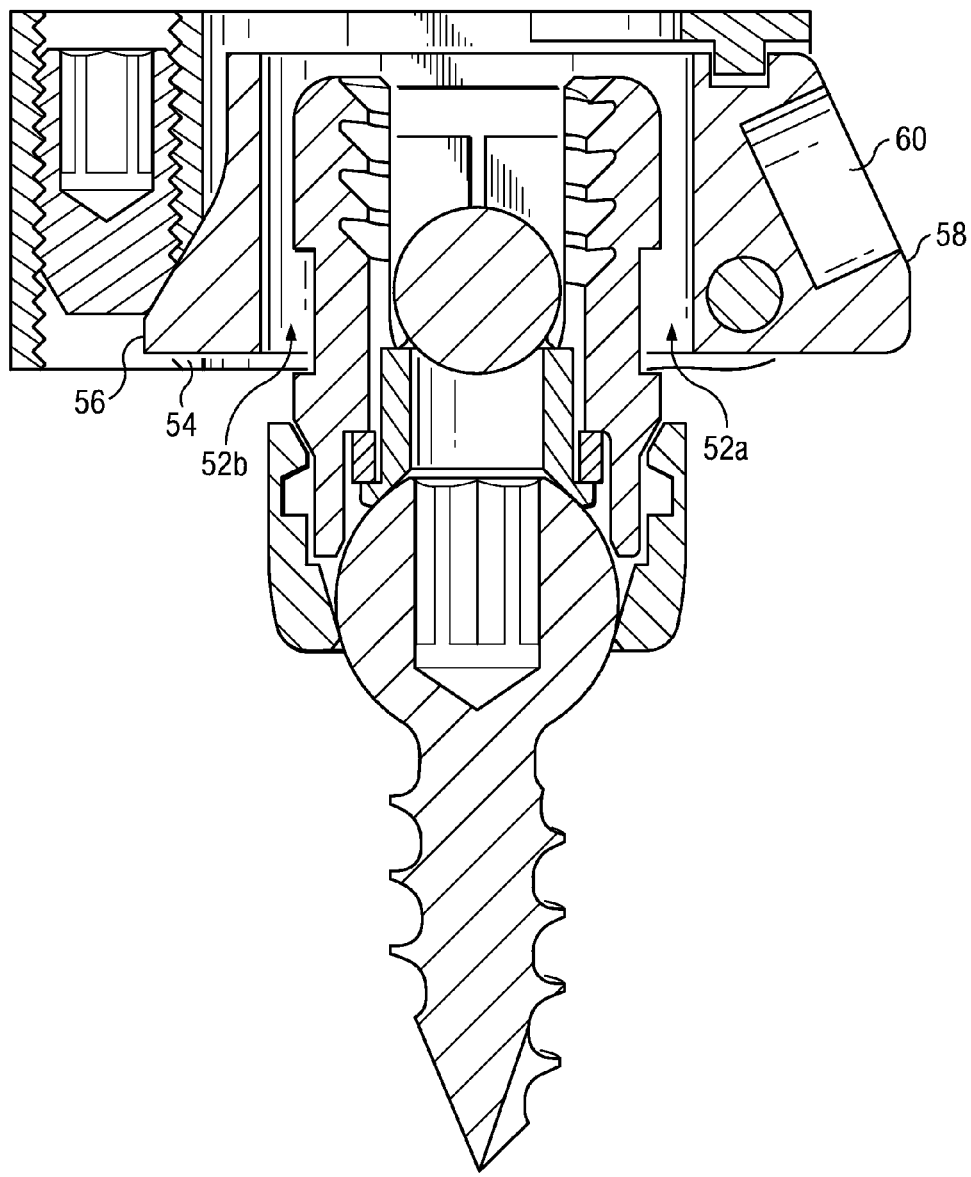
FIG. 5 shows a cross-sectional view of the clamp shown in FIGS. 2-4 attached to a body and rod of the spinal fixation device shown in FIGS. 1A and 1B.

Referring now also to FIG. 5, during a surgical procedure the spinal fixation devices 12 and rods 14 are placed in a configuration such as is shown in FIGS. 1A and 1B. The cross connecting device 20 is then placed over two spinal fixation devices 12 and each clamp 28 is snapped onto a construct rod 14. In order for this to occur, the set screw 36 is partially backed out of the threaded bore 42 to allow the inner body 32 to spring open to accept the rod 14 into the rod-receiving portion 50a of the rod receiving interface 50. The set screw 36 can then be tightened by driving the set screw 36 into the threaded bore 42. As the set screw 36 is threaded into the outer body 30, it eventually contacts the lever portion 56 of the inner body 32. Once the set screw 36 contacts the lever portion 56, the continued driving of the set screw 36 causes the set screw 36 to drive against the lever portion 56 and urge the lever portion 56 to cause the inner body 32 to pivot relative to the outer body 30 about the pin 34. However, the pivoting motion is restricted due to the limiting action of the tab 46 of the outer body 30 against the mating groove 48 of the inner body 32. Thus, continued tightening of the set screw 36 against the lever portion 56 causes the rod-receiving portion 50a to tighten against the rod 14, thereby clamping the clamp 28 onto the rod 14.

The inner body 32 also includes a tapered surface 58 opposite the lever portion 56. The tapered surface 58 includes connection-member-receiving region 60. The connection-member-receiving region 60 is provided for attaching the clamp 28 to a connection member such as one of the first and second connection members 24 and 26 shown in FIGS. 1A and 1B. The mechanism used for attaching a connection member to the clamp 28 can vary, but examples can include press-fitting the connection member into the connection-member-receiving region 60; securing the connection member into the connection-member-receiving region 60 using a set screw, pin, or bolt; and providing corresponding threaded surfaces on the connection member and connection-member-receiving region 60 so that the connection member can be threaded into the connection-member-receiving region 60.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A clamp for attaching a cross connecting device to a spinal fixation system, the clamp comprising:
    an outer body that defines an internally threaded bore and an outer body cavity, the outer body including a clearance slot configured to allow a rod to extend through the outer body cavity;
    an inner body that is at least partially disposed within the outer body cavity, the inner body including a rod-receiving interface configured to receive the rod, and the inner body defining an inner body cavity;
    a pin configured to connect the outer and inner bodies to each other; and
    a set screw configured to be driven into the internally threaded bore to secure the inner body to the spinal fixation system, wherein
    a diameter of the rod-receiving interface is less than a diameter of the clearance slot.

2. The clamp of claim 1, wherein the spinal fixation system includes the rod.

3. The clamp of claim 2, wherein the diameter of the rod-receiving interface is less than a diameter of the rod.

4. The clamp of claim 1, wherein the rod-receiving interface includes a slotted rod-receiving interface.

5. The clamp of claim 4, wherein the slotted rod-receiving interface includes a rod-receiving portion configured to snap onto the rod.

6. The clamp of claim 5, wherein the rod-receiving portion of the slotted rod-receiving interface is configured to be tightened onto the rod as the set screw is driven into the internally threaded bore.

7. The clamp of claim 5, wherein the slotted rod-receiving interface further includes at least one expansion portion.

8. The clamp of claim 1, wherein the outer body includes a slot that extends between the internally threaded bore and the outer body cavity.

9. A clamp for attaching a cross connecting device to a spinal fixation system, the clamp comprising:
    an outer body that defines an internally threaded bore and an outer body cavity;
    an inner body that is at least partially disposed within the outer body cavity, the inner body defining an inner body cavity;
    a pin configured to connect the outer and inner bodies to each other; and
    a set screw configured to be driven into the internally threaded bore to secure the inner body to the spinal fixation system, wherein
    the outer body includes a slot that extends between the internally threaded bore and the outer body cavity, and
    the inner body includes a lever portion that extends through the slot into the internally threaded bore.

10. The clamp of claim 1, further comprising a stop feature configured to limit pivoting movement between the outer and inner bodies about the pin.

11. The clamp of claim 10, wherein the stop feature includes a tab and a mating groove.

12. A spinal fixation system comprising:
    a spinal fixation device body;
    a rod connected to the spinal fixation device body;
    a cross-connecting device; and
    a clamp configured to connect the cross-connecting device to the rod, the clamp comprising:
        an outer body that defines an internally threaded bore and an outer body cavity, the outer body including a clearance slot configured to allow a rod to extend through the outer body cavity;

an inner body that is at least partially disposed within the outer body cavity, the inner body including a rod-receiving interface configured to receive the rod, and the inner body defining an inner body cavity configured to receive at least a portion of the spinal fixation device body;

a pin configured to connect the outer and inner bodies to each other; and a set screw configured to be driven into the internally threaded bore to secure the inner body to the rod, wherein a diameter of the rod-receiving interface is less than a diameter of the clearance slot.

13. The spinal fixation system of claim 12, wherein the rod receiving interface includes a slotted rod-receiving interface.

14. The spinal fixation system of claim 13, wherein the slotted rod-receiving interface includes a rod-receiving portion configured to snap onto the rod.

15. The spinal fixation system of claim 14, wherein the rod-receiving portion of the slotted rod-receiving interface is configured to be tightened onto the rod as the set screw is driven into the internally threaded bore.

16. The spinal fixation system of claim 14, wherein the slotted rod-receiving interface further includes at least one expansion portion.

17. The spinal fixation system of claim 12, wherein the outer body includes a slot that extends between the internally threaded bore and the outer body cavity.

18. The spinal fixation system of claim 12, wherein the clamp further comprises a stop feature configured to limit pivoting movement between the outer and inner bodies about the pin.

19. The spinal fixation system of claim 18, wherein the stop feature includes a tab and a mating groove.

20. The spinal fixation system of claim 12, wherein the inner body is configured to receive at least a portion of the spinal fixation device body.

21. The spinal fixation system of claim 12, wherein the diameter of the rod-receiving interface is less than a diameter of the rod.

22. A spinal fixation system comprising:

a spinal fixation device body;

a rod connected to the spinal fixation device body;

a cross-connecting device; and a clamp configured to connect the cross-connecting device to the rod, the clamp comprising:

an outer body that defines an internally threaded bore and an outer body cavity;

an inner body that is at least partially disposed within the outer body cavity, the inner body defining an inner body cavity configured to receive at least a portion of the spinal fixation device body;

a pin configured to connect the outer and inner bodies to each other; and a set screw configured to be driven into the internally threaded bore to secure the inner body to the rod, wherein the outer body includes a slot that extends between the internally threaded bore and the outer body cavity, and the inner body includes a lever portion that extends through the slot into the internally threaded bore.

* * * * *